US011306283B2

(12) United States Patent
Singer et al.

(10) Patent No.: US 11,306,283 B2
(45) Date of Patent: Apr. 19, 2022

(54) APPARATUS AND A METHOD FOR TRANSFERRING MATERIAL

(71) Applicant: Singer Instrument Company Limited, Somerset (GB)

(72) Inventors: Harry Singer, Somerset (GB); Neil Parbrook, Somerset (GB)

(73) Assignee: Singer Instrument Company, Limited, Somerset (GB)

(*) Notice: Subject to any disclaimer, the term of this patent is extended or adjusted under 35 U.S.C. 154(b) by 988 days.

(21) Appl. No.: 16/308,469

(22) PCT Filed: Aug. 19, 2016

(86) PCT No.: PCT/EP2016/069672
§ 371 (c)(1),
(2) Date: Dec. 9, 2018

(87) PCT Pub. No.: WO2017/045864
PCT Pub. Date: Mar. 23, 2017

(65) Prior Publication Data
US 2019/0169560 A1    Jun. 6, 2019

(30) Foreign Application Priority Data

Sep. 17, 2015  (GB) ..................... 1516473

(51) Int. Cl.
*C12M 1/30*    (2006.01)
*G01N 35/10*    (2006.01)

(52) U.S. Cl.
CPC ............ *C12M 33/02* (2013.01); *G01N 35/10* (2013.01); *G01N 2035/1037* (2013.01)

(58) Field of Classification Search
None
See application file for complete search history.

(56) References Cited

U.S. PATENT DOCUMENTS

| 4,287,301 A | * | 9/1981 | Astle | ........................ C12Q 1/24 435/30 |
| 4,613,573 A | | 9/1986 | Shibayama | |
| 5,063,791 A | * | 11/1991 | Martin | .................... C12M 33/04 73/864.31 |
| 6,309,600 B1 | * | 10/2001 | Hunter | .................. B01F 5/0085 422/504 |

(Continued)

FOREIGN PATENT DOCUMENTS

| DE | 10013513 A1 | 10/2000 |
| EP | 307085 A1 | 3/1989 |

OTHER PUBLICATIONS

International Search Report for PCT/EP2016?069672, dated Oct. 28, 2016. European Patent Office.

(Continued)

*Primary Examiner* — Brian R Gordon

(57) ABSTRACT

An apparatus is provided for transferring materials such as cells or microbial colonies during sample preparation. The apparatus includes a filament having a first end for carrying the materials and a head portion adapted to movably receive at least part of the filament. The filament is movable such that the first end protrudes by a pre-determined length from the head portion to allow transfer of the materials to and from the first end.

14 Claims, 10 Drawing Sheets

(56) References Cited

U.S. PATENT DOCUMENTS

2003/0003596 A1    1/2003  Pawliszyn
2007/0207064 A1    9/2007  Kohara
2009/0246412 A1*  10/2009  Knowles ................ B23K 26/32
                                                                  427/596
2016/0370264 A1*  12/2016  Campbell ............ G01N 1/2813

OTHER PUBLICATIONS

United Kingdom Search Report, dated Jul. 6, 2016. Dr. Richard Wood.

* cited by examiner

APPARATUS AND A METHOD FOR TRANSFERRING MATERIAL

FIELD OF THE INVENTION

The invention relates to an apparatus and a method for transferring material or materials to, from or between sampling containers such as petri dishes, multiwell plates or microwell plates. Particularly, but not exclusively, the material or materials include, but are not limited to, biological materials, chemical regents or the like.

BACKGROUND OF THE INVENTION

During sample preparations in research laboratories as well as industrial laboratory environments, it is always desirable for the sample material such as microbial colonies or cell lines, and/or solvents, solutions or reagents to be transferred in a precise and controlled manner. Recent advances in the relevant technology enable the sampling steps to be conducted automatically, either in part or in full, for high-throughput samplings. The automation allows highly accurate positioning and reproducible picking and/or dispensing of samples to be achieved. The automation also improves efficiency, and allows a much faster and more economical operation during the traditionally time and labour demanding research processes.

A number of tools have been developed for pinning, picking and/or transferring of biological materials of interest such as cell lines and/or microbial colonies. For example, specialised metal pins have been developed for use in automatic or semi-automatic colony pickers for picking microbial colonies from the cultures, with the metal pins being reusable after sterilization. Disposable pin tips have also been developed for similar purposes, with the pin tips being manufactured and arranged in the form of a cassette of tips, and from where the individual tip can be picked up and discarded to avoid contamination. Throughout the sample preparation steps, operation in a sterile condition is often highly critical as any contamination will affect accuracy of the generated data and also spoilage of the biological samples. Traditionally, in a laboratory environment, sterilization can be conducted by, but not limited to, heating, UV-irradiation or washing/rinsing by water or ethanol. Depending on sterility requirement, the sterilization steps vary and can be very much tedious and time consuming, and insufficient sterilization may easily lead to contamination of the samples.

OBJECTS OF THE INVENTION

It is an object of the present invention to overcome or ameliorate at least one of the disadvantages of the prior art, or to provide a useful alternative.

The above object is met by the combination of features of the main claims; the sub-claims disclose further advantageous embodiments of the invention.

One skilled in the art will derive from the following description other objects of the invention. Therefore, the foregoing statement of object is not exhaustive and serves merely to illustrate one of the many objects of the present invention.

SUMMARY OF THE INVENTION

In a first main aspect, the invention provides an apparatus for transferring material. The apparatus comprises a filament having a first end for carrying the material; a head portion adapted to movably receive at least part of the filament; wherein the filament is movable such that the first end protrudes by a pre-determined length from the head portion to allow transfer of the material to and from the first end.

Preferably, the filament includes a second end connected to and accommodated in a storage unit.

Preferably, the storage unit comprises a spool for storing a coil of filament.

Preferably, the filament is movable by a driving mechanism capable of advancing and/or retracting the filament towards and/or away from the head portion.

Preferably, the apparatus further comprises a positioning member adapted to engage the filament for positioning the filament.

Preferably, the positioning member comprises a guide tube to receivably engage at least part of the filament.

Preferably, the positioning member is arranged between the driving mechanism and the head portion.

Preferably, the pre-determined length is of a range of about 1 mm to about 10 mm.

Preferably, the apparatus further comprises a cutting unit adapted to cut or sever a preset length of the filament from the pre-determined length of the filament protruding from the head portion, wherein the preset length is equal to or shorter than the pre-determined length.

Preferably, the preset length to be cut or severed from the pre-determined length is greater than a dip or immersion depth of the first end of the filament.

Preferably, the cutting unit comprises at least one blade for cutting or severing the filament.

Preferably, the apparatus further comprises a transporting mechanism for transporting the head portion.

Preferably, the head portion is adapted to move horizontally along an x-y plane by the transporting mechanism.

Preferably, the head portion is adapted to move vertically along a z-axis by the transporting mechanism.

Preferably, the material to be transferred comprises at least one of a biological material, a chemical substance, a chemical compound and a chemical reagent.

Preferably, the filament is composed of a material selected from a group comprising polymers, metals, glass, ceramic and a combination or a compound thereof.

In a second main aspect, the invention provides a method of transferring material from a source location to a target location. The method comprises arranging a first end of a filament to contact the source location to load the material at the first end. It may include arranging the first end of the filament to contact the target location to unload at least part of the material from the first end. It may further include cutting or severing a length of the filament from the first end to generate a fresh end of the filament which is free of the material. The length of filament cut or severed from the filament may comprise a preset length.

Preferably, the first arranging step comprises positioning the first end of the filament to align with a region of interest at the source location before contacting the source location.

Preferably, the step of contacting the source location comprises touching a surface of the source location by the first end, or dipping or immersing the first end below a surface at the source location. This may include touching a surface of material at the source location or dipping or immersing the first end below a surface of material at the source location.

Preferably, the second arranging step comprises positioning the first end of the filament to align with a region of interest at the target location before contacting the target location.

Preferably, the step of contacting the target location comprises touching a surface of target location by the first end, or dipping or immersing the first end below a surface at the target location. This may include touching a surface of a medium material at the target location, or dipping or immersing the first end below a surface of a medium material at the target location.

Preferably, the first and second arranging steps may comprise moving the first end of the filament from the source location to the target location. Alternatively, the source and target locations may be moved to a position of the filament first end. It will be understood that movement of the first end of the filament may comprise relative movement of the first end of the filament with respect to a location such as the source location, the target location and/or a filament first end cutting or severing location.

Preferably, the cutting step is conducted by at least one of mechanical cutting, mechanical shearing, laser cutting, heat cutting and ultrasonic cutting.

Preferably, the method further comprising a step of advancing the filament towards the first end after the cutting step so as to restore the preset length being cut during the cutting step.

Preferably, the method further comprises a step of movably receiving the filament by a head portion prior to the first arranging step such that the first end protrudes by a pre-determined length from the head portion.

Preferably, the method further comprises a step of positioning the filament by a positioning member prior to the first arranging step.

Preferably, the positioning step comprises receiving the filament within a guide tube.

The summary of the invention does not necessarily disclose all the features essential for defining the invention; the invention may reside in a sub-combination of the disclosed features.

BRIEF DESCRIPTION OF THE DRAWINGS

The foregoing and further features of the present invention will be apparent from the following description of preferred embodiments which are provided by way of example only in connection with the accompanying figures, of which.

DETAILED DESCRIPTION OF THE PREFERRED EMBODIMENTS

The following is a description of preferred embodiments by way of example only and without limitation to the combination of features necessary for carrying the invention into effect.

Reference in this specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

In the claims hereof, any element expressed as a means for performing a specified function is intended to encompass any way of performing that function. The invention as defined by such claims resides in the fact that the functionalities provided by the various recited means are combined and brought together in the manner which the claims call for. It is thus regarded that any means that can provide those functionalities are equivalent to those shown herein.

Figure 1:
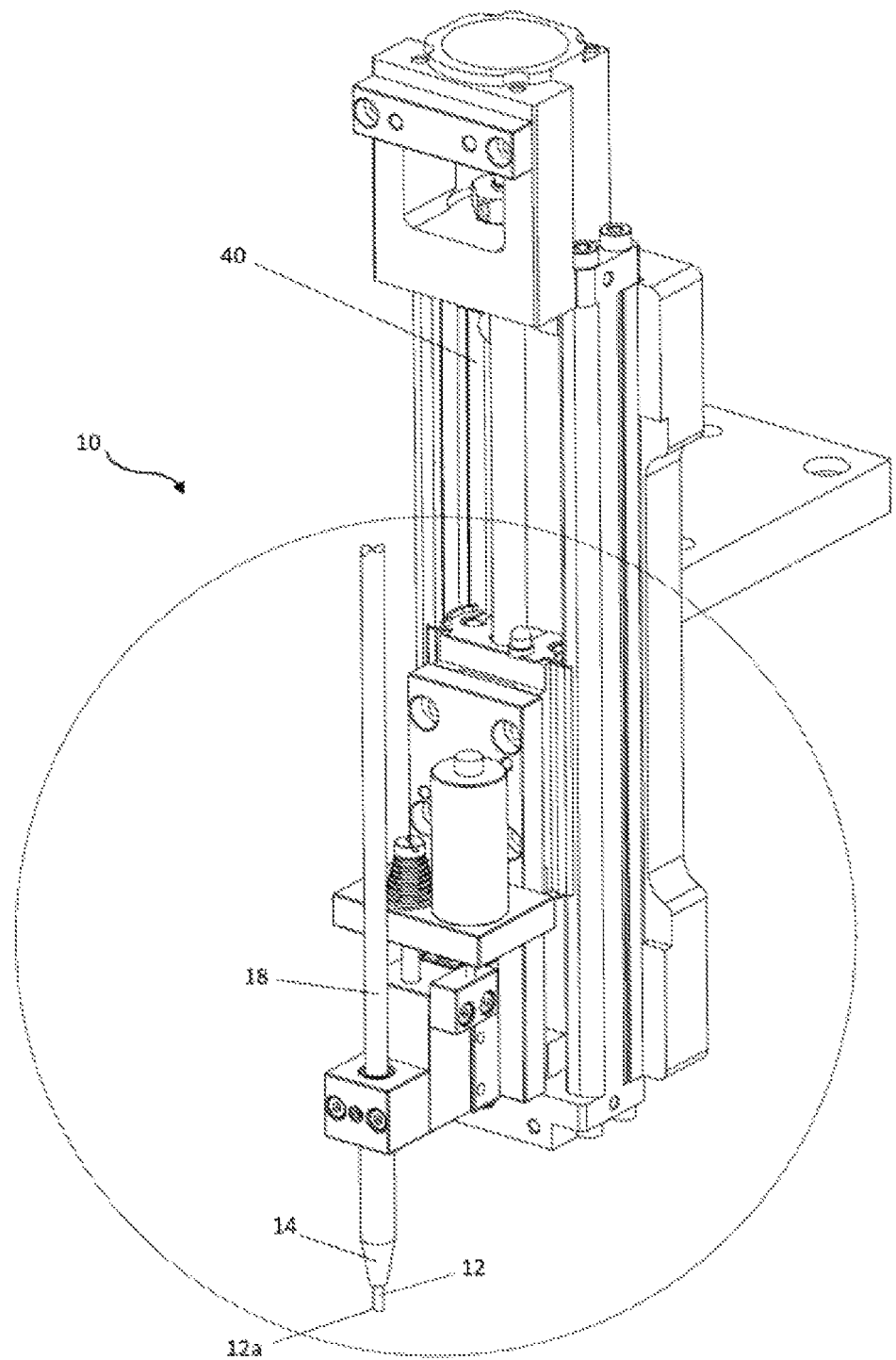
FIG. 1 is a perspective view showing an embodiment of the apparatus for transferring material according to the present invention.

The present invention relates to an apparatus 10 for transferring material or materials, particularly but not exclusively, for transferring at least one of a biological material, a chemical substance including a compound, a solvent and a reagent, and the like during sample preparations which may involve material transfer from, to or between sampling locations such as but not limited to, petri dishes, multi-wells or micro-wells which can be used to contain sample media in solid, set or liquid forms such as agar or culture solution. Referring to FIG. 1, it is shown that the apparatus 10 comprises a filament 12 having a first end 12a for carrying the material of interest, and a head portion 14 adapted to movably receive at least part of the filament 12. The filament 12 is movable such that the first end 12a is capable of protruding by a pre-determined length from the head portion 14 to allow transfer of the material including loading and unloading of the material to and from the first end 12a.

Figure 2:
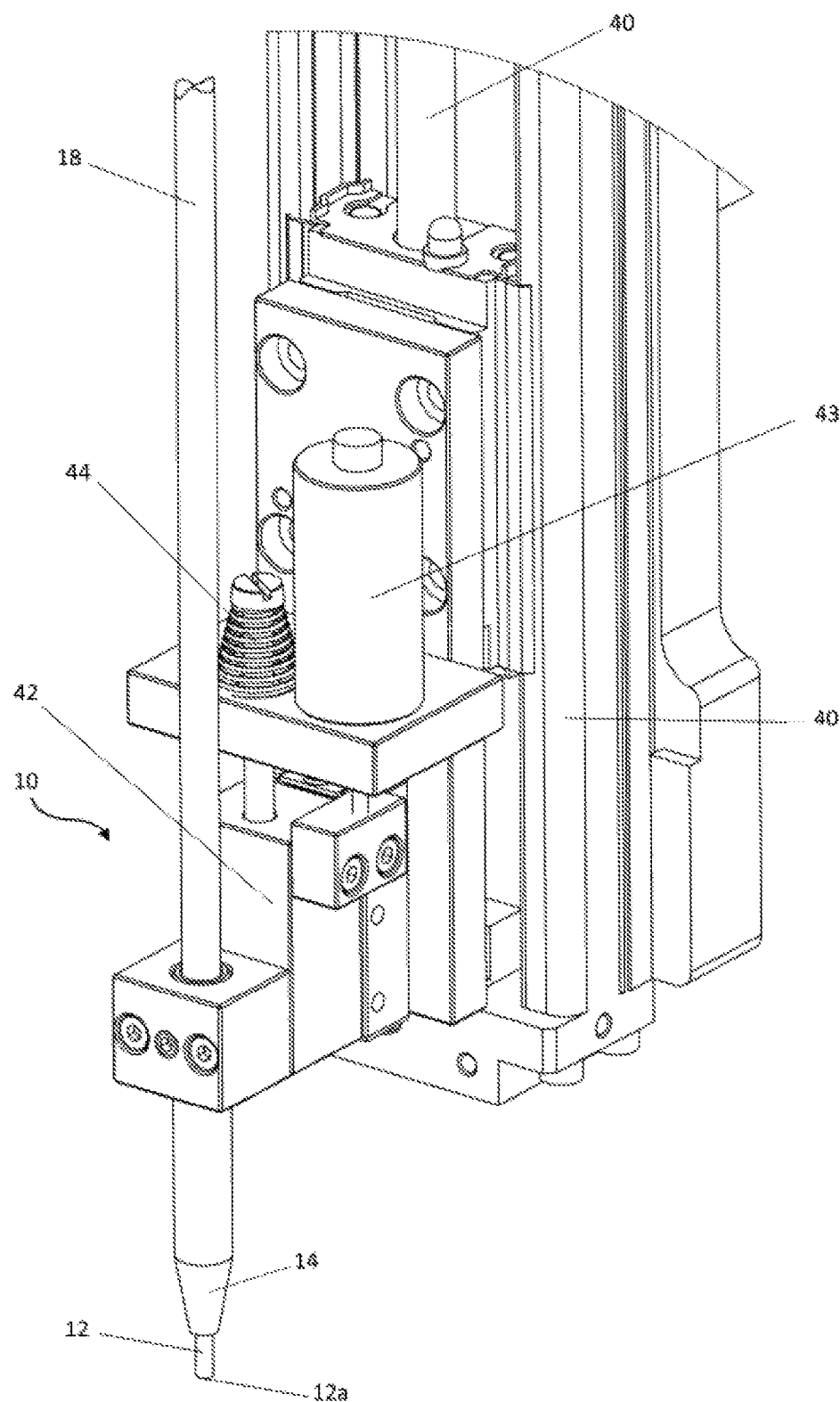
FIG. 2 is a magnified view of the region as shown in the circle of FIG. 1.

FIG. 2 further shows a magnified view of the region of the apparatus 10 indicated by the circle of FIG. 1. As shown in the figure, the filament 12 can be in the form of a fine, continuous threadlike structure having a substantially uniform diameter ranged from, for example, about 0.5 mm to about 3 mm, depending on the requirement of the specific application. The filament may compose of one or more materials selected from a group comprising polymers, metals, glass, ceramic and a combination or a compound thereof. Preferably, for the purpose of transferring microbial colonies, the filament 12 is of about 1 mm in diameter and is made of material such as poly (acrylonitrile-butadiene-styrene), polylactic acid, glass fibre or stainless steel. Properties of the filament can be customised to transfer materials of other natures. For example, for the purpose of transferring liquids such as solvents or chemical reagents in solution forms, volume of liquid transfer will depend on a number of factors including, but not limited to, the diameter of the filament, surface features or morphologies of the filament tip, and/or the hydrophilicity of the filament material. For example, a filament tip of 1 mm diameter made of polycarbonate can be used to transfer liquid with a transferring volume of approximately between 200 to 500 nanolitres per transfer (repeatability of about ±15%).

In one embodiment, the filament 12 is positioned by a positioning member which can be in the form of, for example, a flexible guide tube 18 as shown in the figures. Specifically, the guide tube 18 is arranged between a driving mechanism 20 for driving the filament 12 and the head portion 14. The guide tube 18 is adapted to receivably engage at least part of the filament 12 for positioning and constraining the filament 12 while the filament 12 is driven to move within the guide tube 18. In one embodiment, at least part of the filament 12 is snugly received and is held in position by the guide tube 18. The diameter of the guide tube 18 may be such that, when the filament 12 is received in the guide tube 18, there is sufficient friction between the outer surface of the filament 12 and the inner surface of the guide tube 18 which prevents the filament unintentionally advancing through the head portion 14 until the filament is driven to move through the head portion 14.

Figure 3:
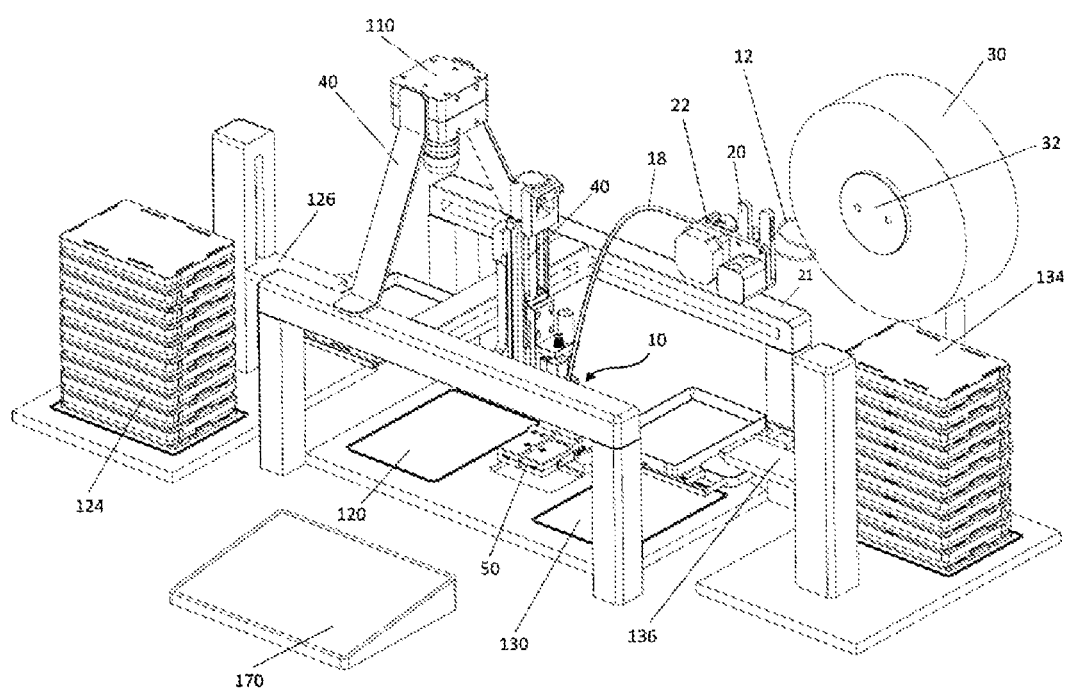
FIG. 3 is a system for transferring material comprising an embodiment of the apparatus of FIG. 1.
Figure 4:
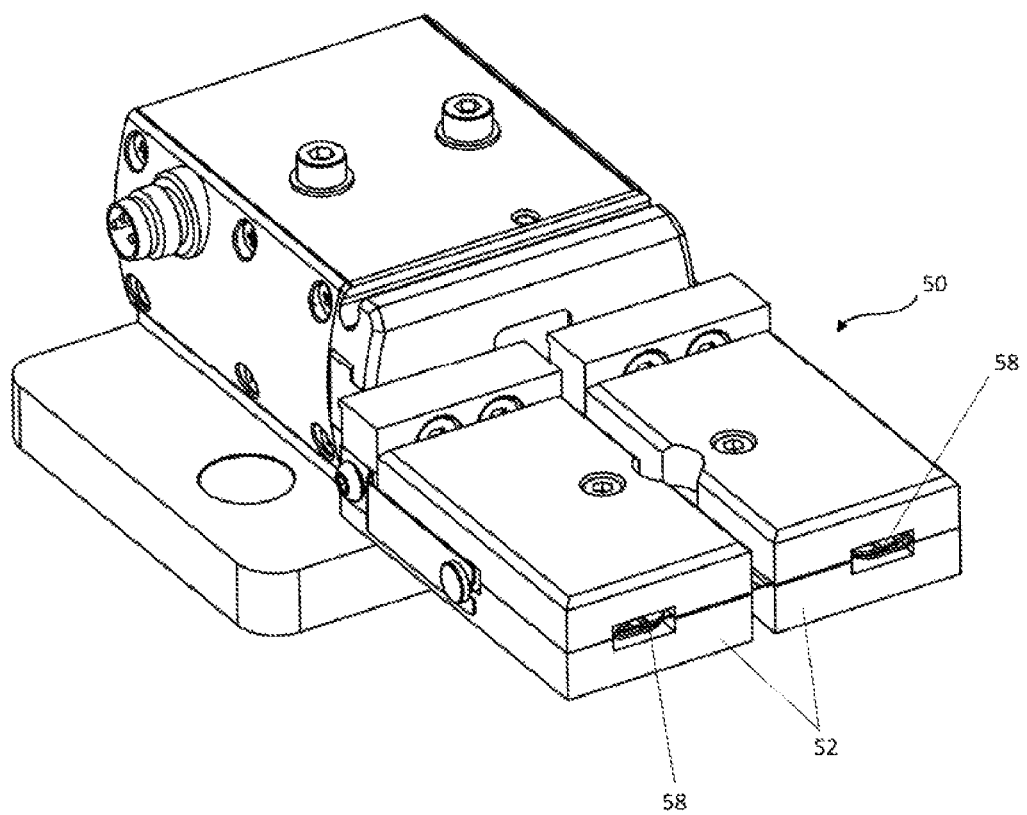
FIG. 4 is a perspective view of a cutting unit as embodied in the present invention showing a closed configuration.
Figure 5:
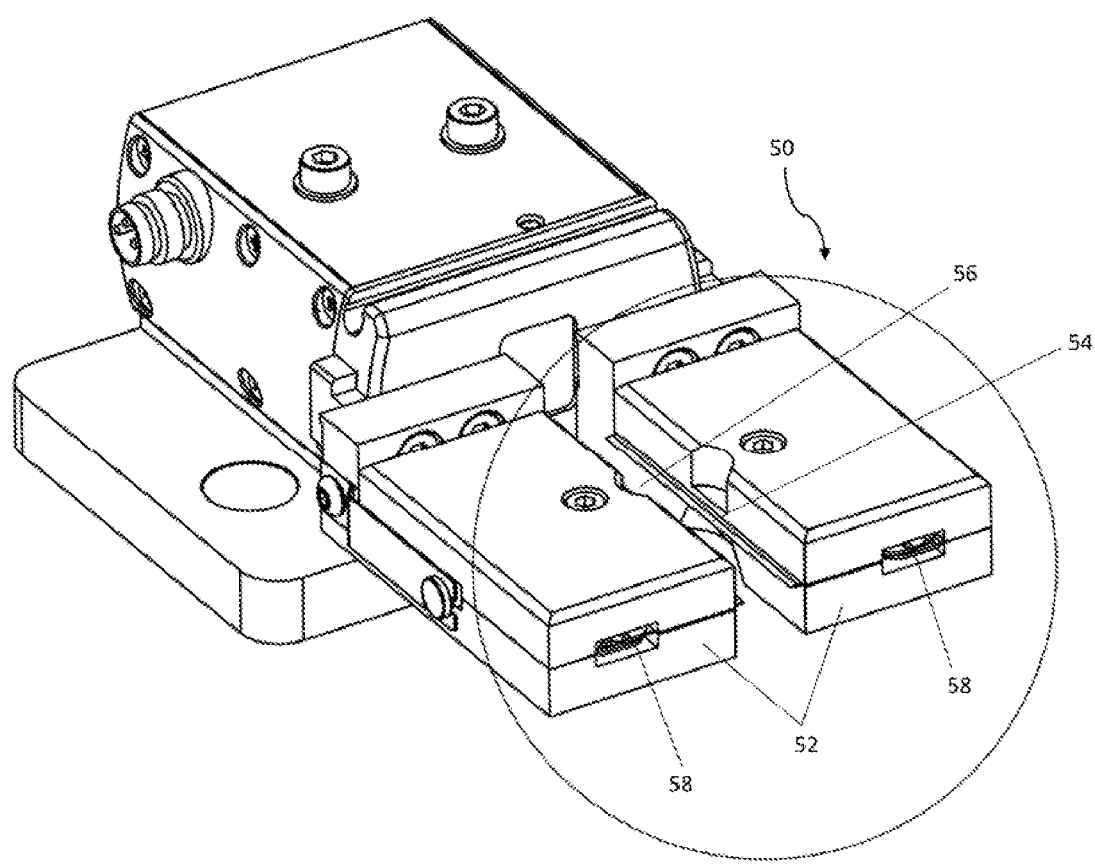
FIG. 5 is a perspective view of the cutting unit of FIG. 4 showing an open configuration.
Figure 6:
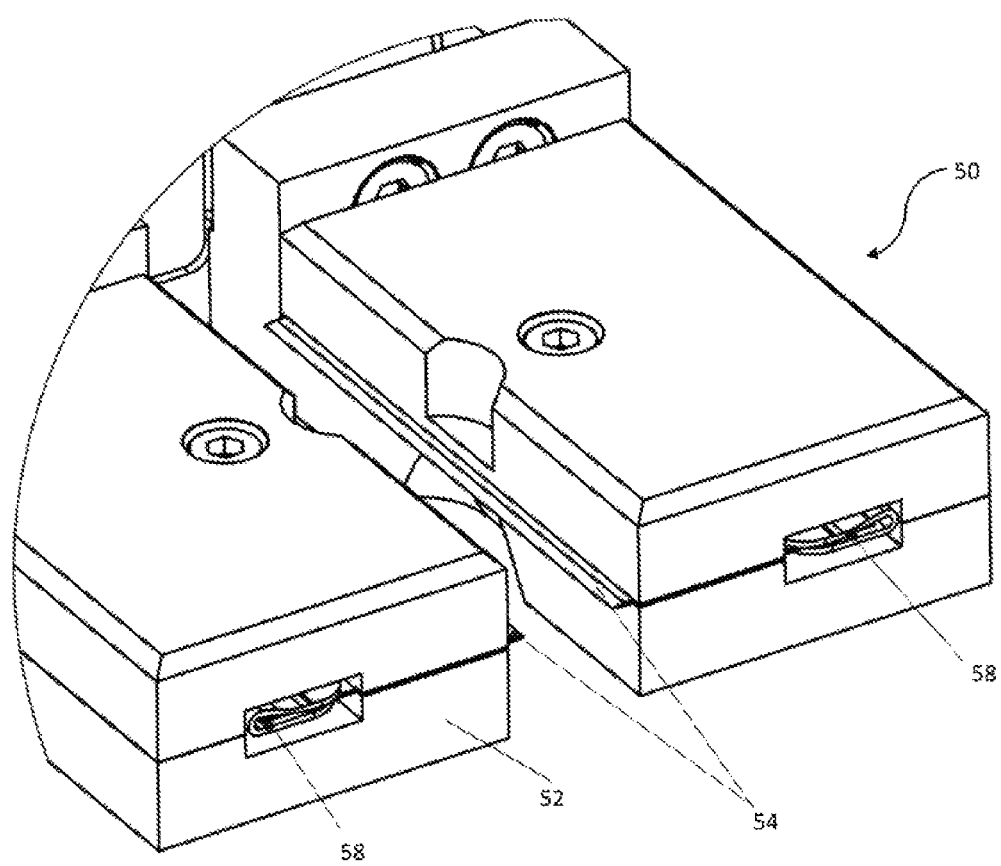
FIG. 6 is a magnified view of the region as shown in the circle of FIG. 5.
Figure 7:
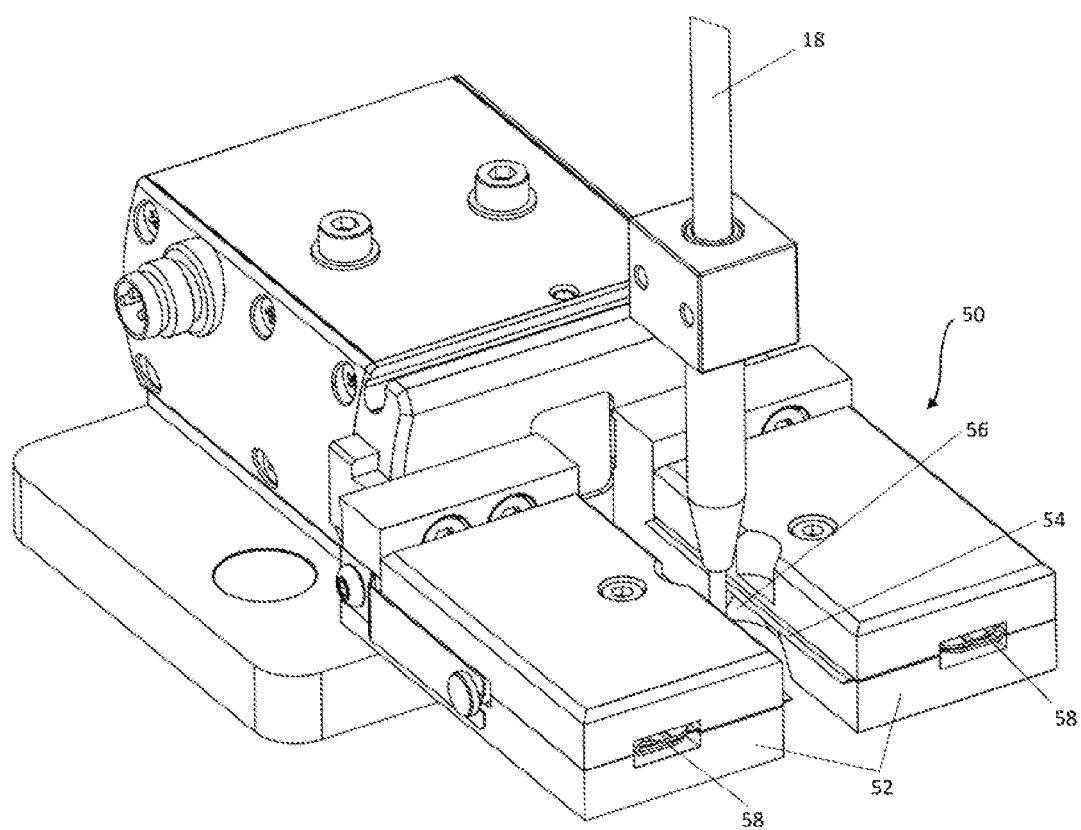
FIG. 7 is a perspective view showing a filament protruded between the blades of the cutting unit of FIG. 4.

The driving mechanism 20, which is best shown in FIG. 3, is capable of advancing and/or retracting the filament 12 towards and/or away from the head portion 14, depending on the operation modes and/or the required functions of the apparatus 10. The driving mechanism 20 is also capable of controlling and adjusting, either finely or coarsely, the amount of protrusion and/or retraction of the filament 12 relative to the head portion 14 for loading, transferring and unloading materials of different natures between various source and target locations.

The apparatus 10 may also comprise a transporting mechanism having at least one transporting arm 40 for transporting components such as the head portion 14, the guide tube 18, and the filament 12 along an x-y horizontal plane and/or vertically along a z-axis so as to align the filament end 12a with a region of interest such as a particular colony at a sampling location. In one embodiment, the transporting arm 40 may comprise a control means such as a floating linear bearing 42 or the like to control and adjust the pressure imposed onto the sampling location when the filament 12 is propagating at different vertical levels so as not to adversely affect the material being picked and also the matrix carrying the material of interest. A solenoid 43 can be used to measure the movement of and/or to control the floating linear bearing 42 so as to allow an accurate cut length of the filament 12, and to prevent any unwanted movement of the floating bearing 42 under dynamic loads. The picking pressure can be further reduced by having a compensating spring 44, and/or be controlled by electrically and/or optically sensing the contact between the end 12a and the target/source location.

FIG. 3 illustrates a material transfer system having an embodiment of apparatus 10 for transferring sample materials between a plurality of rectangular sampling plates, although it is apparent that sampling plates of other common forms such as 60 mm, 90 mm, 100 mm, 150 mm petri dishes, poly (styrene-butadiene-styrene) square plates or multi/micro wells (i.e. microtitre plates) at 48, 96, 384 or 1536 wells density, etc. could also be applicable. The filament 12 of the apparatus 10 may have a second end 12b (not shown) accommodated and connected to a storage unit 30. Particularly, the storage unit 30 can be in the form of, or comprise a spool 32 for storing at least one coil of the filament 12. The storage unit 30 is preferred to be arranged in a fixed position separated from the other components such as the head portion 14, the filament 12, and the driving mechanism 20 so as to reduce the weight imposed thereon which may otherwise affect the stability of the filament 12. Similarly, it is also preferred for the driving mechanism 20 to be arranged in a fixed support 21 separated from the head portion 14 and the filament 12 so as to reduce or avoid any undesirable movement of the filament 12 by the driving mechanism 20 in operation which may potentially affect the precision of the transfer.

The portion of the filament 12 which extends out of the storage unit 30 is held firmly by one or more wheels of a filament feeder 22 of the driving mechanism 20. The filament 12, after leaving the filament feeder 22, is received by the flexible guide tube 18. The guide tube 18 can be fixed at one end at the driving mechanism 20, and connected with the head portion 14 at the other end. The filament 12, being received and held in place by the guide tube 18 and the head portion 14, will function as a picking head movable by one or more transporting arm 40 along the x-y plane and/or the z-axis b for transferring material between a source plate 120 and a target plate 130, which both are located on a first support surface as shown in FIG. 3. The guide tube 18 can be of a sufficient length to span from the driving mechanism 20 to the furthest point of travel of the picking head. Because the guide tube 18 constrains the filament 12 by frictional engagement between the circumferential wall or surface of the filament 12 and the inner surface of the guide tube 18, movement of the filament end 12a relative to the head portion 14 over the course of transfer is substantially not noticeable. Specifically, the tighter the filament 12 fit within the guide tube 18, the smaller any relative movement between the two may be, but also the greater the friction that will be generated and thus, an increased feeding force is required to advance or retract the filament 12 by the feeder 22.

Alternatively or additionally, the positioning and constraining of the filament 12 may also be provided by the frictional force between the filament 12 and the head portion 14. The filament 12 and the guide tube 18 may further be held or supported by any other suitable mechanical holding or locking means, as long as it is considered applicable and appropriate for the present invention.

The pre-determined length of the filament 12 protruding from the head portion 14 is adjustable by controlling the advancing and/or the retracting movement of the filament 12 by the feeder 22 of the driving mechanism 20. In one embodiment, the pre-determined length is of a range from about 1 mm to about 10 mm, depending on the nature of the transferred materials and/or operations of the apparatus 10. For example, for pinning/picking and transferring materials to and/or from solid agar containing sample plates, it is preferred that the protruded, predetermined length is of about 3 mm to about 5 mm from the head portion 14. Whilst for pinning and transferring materials to and/or from liquid medium such as culture solution in microwells, the protruded length can be extended to about 8 mm to about 10 mm so that a sufficient length from the end 12a can be dipped or immersed into the solution to facilitate the loading and unloading of the materials. In this connection, it would be understandable that the pre-determined length of the filament 12 should not be limited to any specific length or range of lengths, but a skilled person would appreciate that the pre-determined length can be varied according to the nature of the material to be transferred, specific setup of the experiment, and also the required application of the apparatus 10 so as to achieve an optimum material transfer.

The apparatus 10 further comprises a cutting unit 50 for cutting or severing a preset length of the filament 12 from the pre-determined length of the filament 12 protruding from the head portion 14 to thereby remove and dispose of the used, contaminated filament end which has previously been in contact with the transferred material. The preset length being cut can be substantially equal to, or shorter than the pre-determined length protruding from the head portion 14. The cutting unit 50 is adapted to cut or sever, and subsequently discard the contaminated filament end 12a to generate a fresh end which is free of the transferred material. The same filament 12, which now, in effect, has a "sterilised" first end after the cut, will then be ready for the next cycle of material transfer.

The apparatus of the present invention is advantageous in that the same filament can be utilised for multiple cycles of transfer without the need of sterilizing the filament or other parts of the apparatus with traditional techniques such as washing by alcohol, steam heating or UV irradiation. Instead, the filament end will be simply cut off and discarded to generate a fresh, sterile end for the next transfer cycle. No replacement of the filament after each transfer is required, but only until the spool of filament is depleted. This allows a more streamlined sample preparation process, with higher controllably and efficiency. Structures of the cutting unit 50 are best illustrated in FIGS. 4 to 7, which show an embodiment of the cutting unit 50 in a closed configuration (see FIG. 4) and an open configuration (see FIGS. 5 to 7). As shown in the figures, the cutting unit 50 may comprise a cutting station 52 having two mounting stages movable towards/away from each other to define a gap 56. A pair of horizontally arranged, counter-propagating razor blades 54 are mounted, one at each of the two respective mounting stages, for cutting the filament 12 from the end 12a when it is extended into the gap 56. Particularly, a preset length from the pre-determined length of the filament 12 will be cut, with the preset length preferred to be greater than the dip/immersion depth from the first end 12a of the filament 12. This is to allow a sufficient distance between the cut and the transfer tip so as to prevent any potential contamination of the blades 54.

The mounting stages of the cutting station 52 can be operated mechanically or electrically to move between the open configuration and the closed configuration. In the open configuration, the two stages are arranged to stay apart so that the filament 12 can be extended into the gap 56. In the closed configuration, the two stages are arranged to move towards each other to bring the blades 54 together thereby cutting the filament end 12a. The blades 54 can be mounted at the cutting station 52 by any known means such as, but not limited to, mounting clips 58 as shown in the figures. It would be appreciated that other means of cutting such as, but not limited to, mechanical shearing by one blade, laser cutting, heat cutting or ultrasonic cutting or the like, should also be encompassed.

After the preset length is cut off by the action of the cutting unit 50, it is preferred that a residual length of about 2 mm of the filament 12 is left to protrude from the head portion 14. The amount of this residual length can be varied by adjusting the position of the filament 12 along the z-axis prior to and/or after the cutting, which is controllable by the driving mechanism 20. Particularly, the preferred amount of the preset length is adjustable based on the requirement of different picking applications. For example, for transferring microbial colonies from/to agar plates, pinning can be done by touching the filament end 12a with the agar where the colonies are located. The microbial materials may generally stick to the cross-sectional tip of the filament end 12a after pinning. However, when the pinning is from large, deep colonies, the microbial materials may potentially adhere up to a height of the circumferential side wall or surface of the filament 12 from the end 12a. Accordingly, for transferring materials to/from solid matrices, cutting of the filament 12 from about 3 to 5 mm from the tip of the filament end 12a would generally be sufficient to generate a sterile, fresh tip and also to avoid contamination of the cutting blades 54. However, for transferring materials to/from liquid media such as culture solutions, there is a higher chance for the picked materials to adhere to the filament's side wall up to a height equivalent to the submerged depth of the filament 12 into the solution or even higher where surface tension creep occurs. Accordingly, cutting of about 3 to 5 mm further up from the submerged depth would therefore be desirable so as to avoid any potential contamination. In general, the shorter is the preset length of the filament being cut, the higher is the risk of contamination of the fresh filament end and/or the blades; whereas the longer is the filament being cut, the quicker will the filament spool be depleted.

Figure 9:
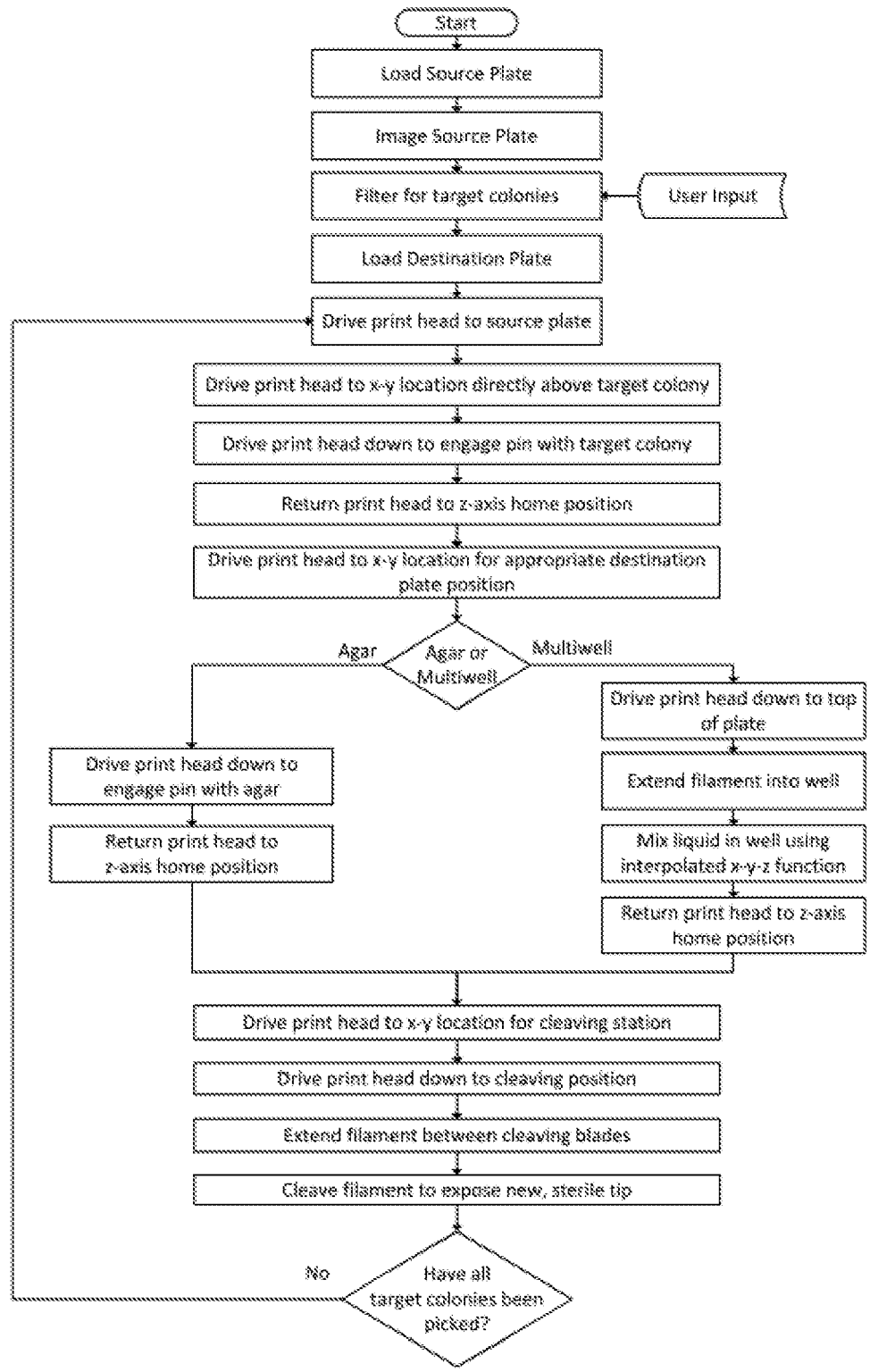
FIG. 9 is a flow diagram showing an embodied work flow of the system of FIG. 3.

Referring to FIG. 9, there is shown a flow diagram illustrating the work flow of the embodied system of FIG. 3. In one embodied operation, prior to the pinning or picking of a material of interest such as a targeted microbial colony or cells material from a source plate, one or more source plates 120 will be transferred from a source storage 124 (which comprises a stack of source plates as shown in this embodiment) to a predetermined source location. The specific position of the targeted material at the source plate 120 will be observed, imaged and/or monitored by a camera 110, which can be supported and/or transported by the transporting arm 40. Similarly, one or more target plates 130 can also be transferred from a target storage 134 to a predetermined target location prior to or after the targeted material is picked from the source plate 120. The source plate 120 and the target plate 130 can be transferred from their respective storages 124 and 134 to the corresponding locations by any transporting means such as robotic arms 126 and 136, which can be operated and/or controlled automatically by a computer program and/or by a user with instruction input via a user interface 170.

In one exemplified process, after the source plate 120 is transferred to or loaded at the predetermined source location, an image recognition software of the camera 110 will allow the user to filter and to identify the target colony of interest. The filtering and identifying steps can be conducted based on any filtering criteria which may include, but not limited to, the size, colour, shape and fluorescence of the targeted colonies or cells. Alternatively or additionally, the filtering and identifying steps can also be fully automatic and be controllable by a computer program. According to identified location of one targeted colony, the head portion 14 will then be driven horizontally along the x-y plane to align the filament end 12a with the targeted colony, and subsequently, be descended along the z-axis to engage the targeted colony so as to load the cell material of interest at the filament end 12a.

After pinning of the targeted colony, the head portion 14 will then be driven horizontally to the target plate 130 where the picked up cell material will be unloaded from the filament end 12a. Particularly, if the target plate 130 is a microbial-carrying, solid agar plate, the head portion 14 will be driven downwardly along the z-axis until the filament end 12a touches with the colony of interest at the agar surface; whereas if the target plate 130 is a microtiter plate filled with cells in liquid medium, after the head portion 14 is descended to a position adjacent the specific well, the filament end 12*a* will advance further down from the head portion 14 so that the end 12*a* can be immersed or dipped into the liquid medium, i.e. below the solution surface of the medium. Optionally, the filament end 12*a* extended into the well may vibrate slightly along the x-y plane and/or the z-axis, or stir the liquid within the well, so as to ensure that the pinned material is sufficiently unloaded and/or mixed well into the liquid medium. After this unloading step, the head portion 14 will retrieve upwardly to a home position.

Although the source and the target plates 120, 130 as illustrated in FIG. 3 are horizontally positioned with the material of interest arranged to be exposed upwardly, it should be appreciated that the plates (such as solid agar plates) can also be positioned in other orientations such as sideway or even upside down as long as it is applicable. In addition, in yet a further embodiment, an alternative arrangement can be made to keep the head portion 14 in a fixed, stationary position while having the source and target plates movable relative to the stationary head portion 14 to load and unload the material of interest.

After the transfer of material from the source plate 120 to the target plate 130, the filament 12 will be subsequently directed to the cutting unit 50 for the "sterilization", i.e. cutting, step where a preset length of the filament 12 will be cut so as to generate a clean, sterile tip for the next pinning operation. Particularly, the head portion 14 will be transported by the transporting arm 40 to a position above the cutting unit 50, and then be driven downwardly to an appropriate cutting position between the blades 54 so that the preset length of filament 12 can be cut by the blades 54. In one embodiment, while the head portion 14 is stopped at a required position above the cutting unit 50, the filament 12 will be driven to advance further down into the gap 56. This is to allow a sufficient distance between the blades 54 and the head portion 14 in order to minimise the chance of contamination. In one further embodiment, the cutting process may comprise a further step of advancing the filament 12 towards the cut end after the cutting is completed to restore the predetermined length of the filament 12 after the preset length is removed. A fresh, clean and sterile filament tip will thus be generated after the cutting process, and the cycle will then repeat for picking another material of interest, either from the same source plate or a different source plate.

Figure 8:
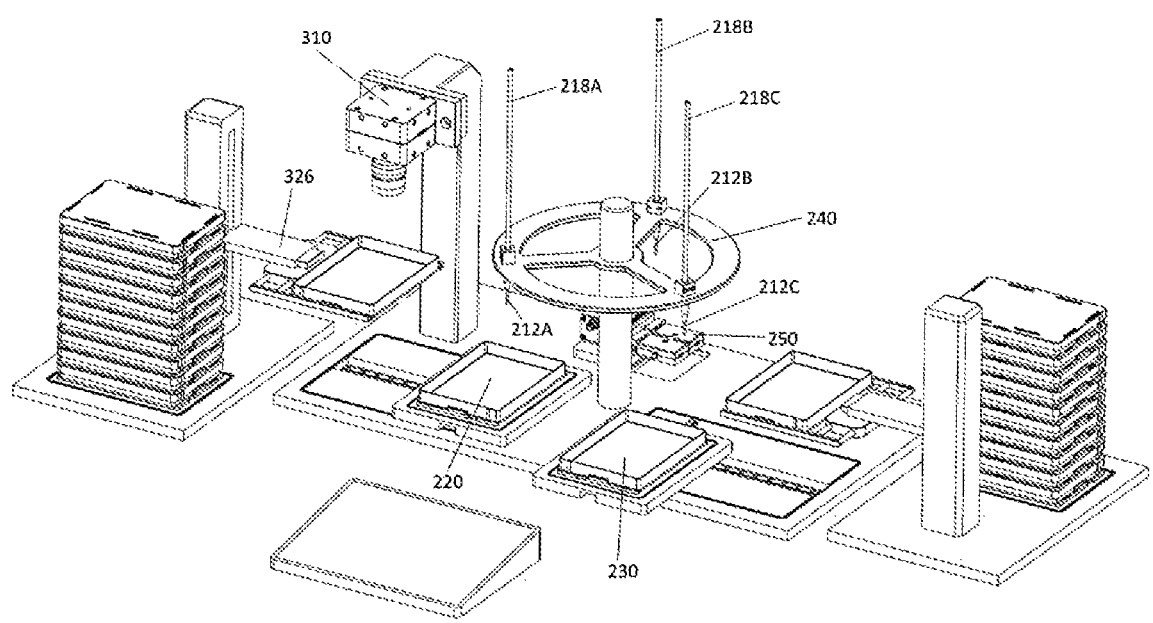
FIG. 8 is a perspective view showing another embodiment of the system of FIG. 3.

Referring to FIG. 8, there is shown another embodied system for transferring material which comprises the apparatus according to the present invention. In this embodiment, three picking filaments 212A, 212B, 212C are mounted in parallel on a common, rotatable transporting wheel 240 in a radially spaced arrangement. The transporting wheel 240 is capable of moving vertically along a central axis and also rotatably about the central axis, thereby transporting the mounted filaments vertically and also circularly in a controlled manner.

Each of the filaments 212A, 212B, 212C can be configured and arranged in a substantially similar manner as to what has been described in the previous embodiments. Particularly, each of the filaments 212A, 212B, 212C can be configured to be receivably engaged by a corresponding flexible guide tube 218A, 218B, 218C, and that a first end of each of these filaments can be driven by one or more driving or feeding mechanisms (not shown) to protrude from the corresponding head portion 214A, 214B, 214C for a predetermined length to facilitate loading and unloading of the material of interest from/to the source/target plates. However, instead of having a transporting arm 40 for transporting one filament at a time, the transporting wheel 240 is now in place to carry and move three filaments such that the loading, unloading of the material, and also cutting of the filament end for "sterilization" can be conducted simultaneously by the respective filaments 212A, 212B, 212C in one single operation cycle, which significantly increases throughput and thus efficiency of the experimental procedure.

It would be appreciated that an alternative arrangement such as by keeping the transporting wheel 240 in a fixed, stationary position while having the source plate, the target plate and the cutting unit movable, for example, on a common rotating stage, relative to the stationary wheel, should also be encompassed.

Figure 10:
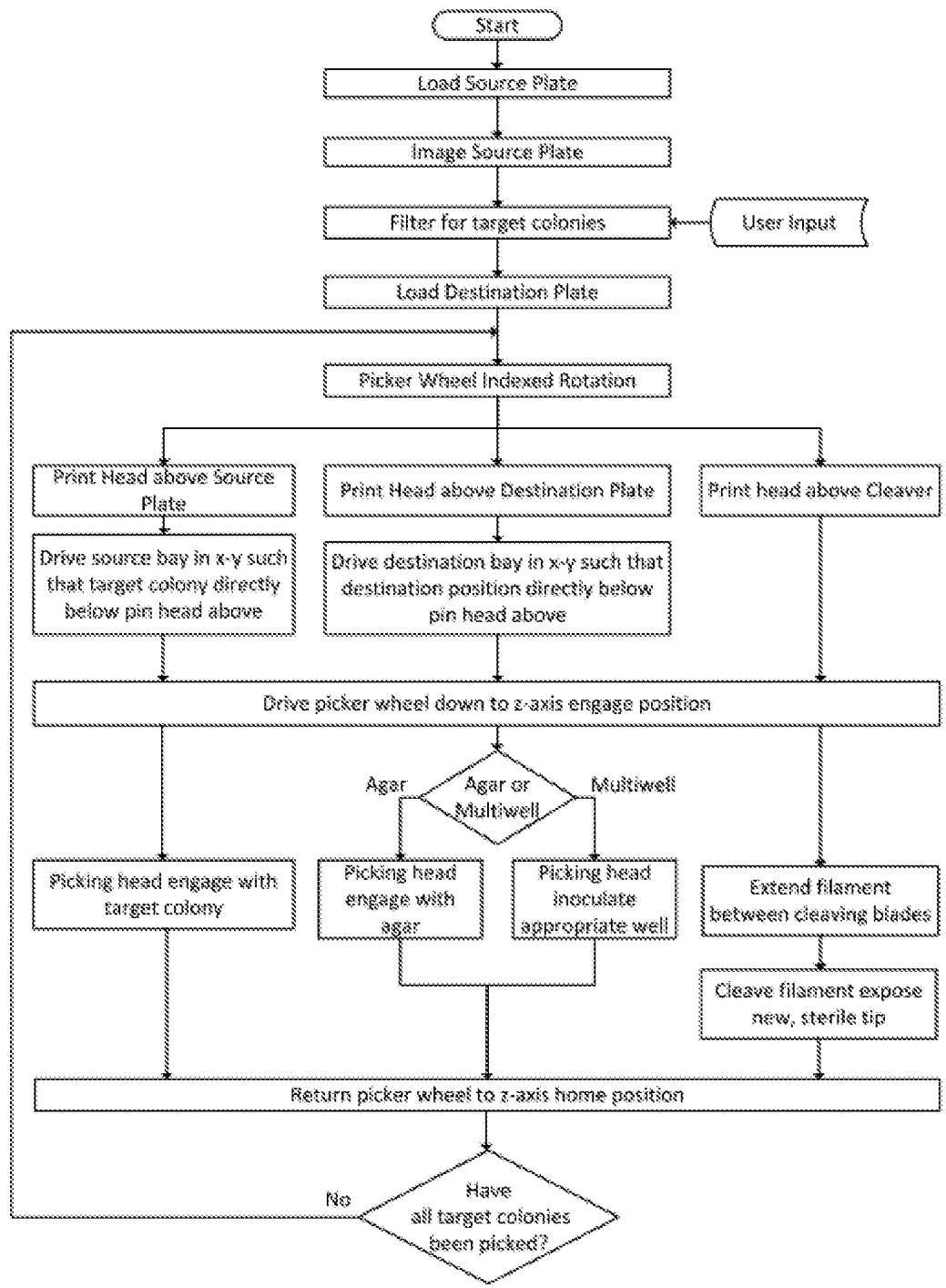
FIG. 10 is a flow diagram showing an embodied work flow of the system of FIG. 8.

A flow diagram illustrating an exemplified work flow of the system of FIG. 8 is shown in FIG. 10, which is in general similar to the steps as shown in FIG. 9. Particularly, after the source plate 220 is loaded at the predetermined source location, the transporting wheel 240 will be rotated about 120 degrees about its central axis to position, for example, the filament 212A which has a fresh, sterile end 212A*a*, above the source plate 220. As described earlier, a camera 310 can be used to observe, image and thus align the filament end 212A*a* with a targeted colony at the source plate 220. The alignment between the filament end 212A*a* and the targeted colony can further be assisted by movement of robotic arm 326, which is capable of coarsely changing and/or finely adjusting location of source plate 220. After the colony identification and/or alignment between the filament 212A and the colony of interest, the transporting wheel 240 will be lower for a required distance to allow pinning of the colony by the filament end.

Concurrently, the filament 212C, which tip has presumably been loaded in a prior operation with cell/microbial material in the previous cycle, will also be lowered to engage the target plate 230 to unload the carried material. Similar to the previous embodiments, if the target plate 230 is an agar plate, the filament end 212C*a* can be arranged to engage the agar plate at its surface. Alternatively, if the target plate 230 carries sample in solution form within one or more wells, the filament end 212C*a* can be arranged to advance further to immerse into the solution of the well.

Similarly, during the loading and unloading steps concurrently occurred at the filaments 212A and 212C, the contaminated end of the filament 212B will be extended into and be cut off by a cutting unit 250 so as to expose a new, sterile tip of the filament for the next picking cycle.

After the respective loading, unloading and cutting steps are completed at the corresponding locations, the transporting wheel 240 will move upward to be restored to its home position. The source/target plates 220/230 will be removed and be replaced by a new source plate and a new target plate (if required). The transporting wheel 240 will then be rotated by another 120 degree to align the filament 212B, which now includes a freshly cut, sterile tip ready for picking, with the new sourced plate, and to align simultaneously the filament 212C with the cutting unit 250 for cutting the used filament end from the earlier cycle. The operation cycle then repeats until the end of the sample preparation procedure.

The invention claimed is:

1. An apparatus for transferring material, comprising:
   a first support surface;
   a head portion that includes and guides a part of a filament, said filament being movable relative to said head portion and having a first end protruding from the head portion for carrying the material to be transferred from a sampling location to a target location both located on the first support surface;

at least one transporting arm connected to the first support surface and the head portion; the at least one transporting arm configured for transporting the head portion along an x-y horizontal plane of the apparatus and/or vertically along a z-axis of the apparatus to align the first end of the filament with the sampling location or the target location;

a driving mechanism in contact with the filament and configured for driving the filament such that the first end of the filament moves towards or away from the head portion, the driving mechanism mounted in a fixed position on a fixed position support of the apparatus that is connected to the first support surface and which does not move with the head portion;

wherein the filament is movable relative to the head portion such that the first end protrudes from the head portion to allow transfer of the material to and from the first end; and a cutting unit on the first support surface and configured for cutting or severing a length of the filament from the first end of the filament protruding from the head portion.

2. The apparatus according to claim 1 further comprising a storage unit, wherein the filament includes a second end connected to and accommodated in the storage unit.

3. The apparatus according to claim 2, wherein the storage unit comprises a spool storing a coil of the filament comprising said second end of the filament.

4. The apparatus according to claim 2, wherein the storage unit is arranged in a fixed position and supported by a second surface on the apparatus such that the storage unit does not move with the head portion.

5. The apparatus according to claim 1 further comprising a guide tube guiding a part of the filament.

6. The apparatus according to claim 5, wherein the guide tube is connected between the driving mechanism and the head portion.

7. The apparatus according to claim 1, wherein the cutting unit is arranged in a fixed position on the first support surface such that the cutting unit does not move with the head portion.

8. The apparatus according to claim 1, wherein the cutting unit comprises at least one blade for cutting a length from the first end of the filament.

9. The apparatus according to claim 1, wherein the filament is composed of a material selected from a group consisting of polymers, metals, glass, ceramic and a combination or a compound thereof.

10. The apparatus according to claim 1, wherein the head portion includes a floating linear bearing configured to control and adjust pressure imposed onto the sampling location by the first end of the filament when the first end of the filament is propagating at different vertical levels.

11. The apparatus according to claim 10, wherein the head portion includes a solenoid configured to control the floating linear bearing to prevent unwanted movement of the floating linear bearing under dynamic loads.

12. The apparatus according to claim 5, wherein the guide tube comprises a flexible guide tube.

13. An apparatus for transferring material, comprising:
a first support surface
a head portion that includes and guides a part of a filament, said filament being movable relative to said head portion and having a first end protruding from the head portion for carrying the material to be transferred from a sampling location to a target location both located on the first support surface;

at least one transporting arm connected to the first support surface and the head portion; the at least one transporting arm configured for transporting the head portion along an x-y horizontal plane of the apparatus and/or vertically along a z-axis of the apparatus to align the first end of the filament with the sampling location or the target location; and a cutting unit on the first support surface and configured for cutting or severing a length of the filament from the first end of the filament protruding from the head portion;

wherein the filament is movable such that the first end protrudes from the head portion to allow transfer of the material to and from the first end; and wherein the head portion includes a floating linear bearing configured to control and adjust pressure imposed onto the sampling location by the first end of the filament when the first end of the filament is propagating at different vertical levels.

14. A method of transferring material from a source location to a target location on a first support surface of an apparatus, said apparatus comprising: a head portion including and guiding a part of a filament, said filament being movable relative to said head portion and having a first end protruding from the head portion for carrying the material to be transferred from the sampling location to the target location; at least one transporting arm connected to the first support surface and the head portion; the at least one transporting arm configured for transporting the head portion along an x-y horizontal plane of the apparatus and/or vertically along a z-axis of the apparatus to align the first end of the filament with the sampling location or the target location; and a driving mechanism in contact with the filament and configured for driving the filament such that the first end of the filament moves towards and away from the head portion, the driving mechanism mounted in a fixed position on a fixed position support of the apparatus that is connected to the first support surface and which does not move with the head portion; wherein the filament is movable relative to the head portion such that the first end protrudes from the head portion to allow transfer of the material to and from the first end; and a cutting unit for cutting or severing a length from the first end of the filament protruding from the head portion, the method comprising using the apparatus to perform the steps of:

contacting the first end of the filament protruding from the head portion with the source location to load the material at said first end;

moving the first end of the filament away from the source location and contacting the first end of the filament with the target location to unload at least part of the material from the first end at said target location; and using the cutting unit, cutting a length of the filament from the first end to provide an end of the filament, which is free of the material;

wherein the step of moving does not include moving: (i) the driving mechanism and/or (ii) a storage unit storing a second end of the filament.

* * * * *